United States Patent [19]

Imanishi et al.

[11] Patent Number: 5,059,612
[45] Date of Patent: Oct. 22, 1991

[54] ANTI-DEMENTIA DRUG

[75] Inventors: Taiichiro Imanishi; Yasuyuki Ichimaru; Aiko Sawa; Fukio Konno, all of Yokohama, Japan; Helmut Wachtel, Berlin, Fed. Rep. of Germany; Showa Ueki, Fukuoka, Japan; Michihiro Fujiwara, Fukuoka, Japan; Tsuneyuki Yamamoto, Fukuoka, Japan

[73] Assignee: Schering Aktiengesellschaft, Berlin and Bergkamen, Fed. Rep. of Germany

[21] Appl. No.: 578,655

[22] Filed: Sep. 7, 1990

[30] Foreign Application Priority Data

Dec. 11, 1989 [JP] Japan ................................. 1-318818

[51] Int. Cl.$^5$ ............................................. A61K 31/41
[52] U.S. Cl. ..................................................... 514/359
[58] Field of Search .......................................... 514/359

[56] References Cited

U.S. PATENT DOCUMENTS

| | | | |
|---|---|---|---|
| 4,012,495 | 3/1977 | Schmiechen et al. | 424/274 |
| 4,153,713 | 5/1979 | Huth et al. | 424/274 |
| 4,193,926 | 3/1980 | Schmiechen et al. | 260/326.5 S |

OTHER PUBLICATIONS

Horowski et al., "Clinical Effects of the Neurotropic Selective cAMP Phosphodiesterase Inhibitor Rolipram in Depressed Patients . . . ", Curr. Therap. Res. 38:23-29, Jul. 1985.

Primary Examiner—Stanley J. Friedman
Attorney, Agent, or Firm—Millen, White & Zelano

[57] ABSTRACT

The invention relates to a method of treating dementia, such as cerebro-vascular dementia, for example, multiple infarct dementia and amyloid angiopathic dementia, cerebro-parenchymatous dementia, such as Alzheimer's dementia and Pick's disease, and dementia caused by brain tumor, hydrocephalus, hepatic meningitis, cerebral trauma, or cerebral function disorders, comprising administering rolipram.

8 Claims, No Drawings

ANTI-DEMENTIA DRUG

SUMMARY OF THE INVENTION

The present invention relates to an anti-dementia agent which comprises rolipram (4-[3-cyclopentyloxy)-4-methoxyphenyl]-2-pyrrolidinone) as an active ingredient.

As the proportion of aged people grows larger in the society, countermeasures against senile dementia causes by cerebral function disorders have become a serious social problem. A variety of drugs have been developed as anti-dementia agents. However, a sufficiently effective drug has not been obtained yet.

Rolipram is represented by the following formula:

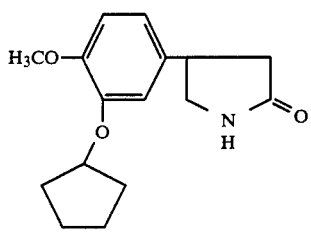

(I)

and is known to have antagonistic activity against apormorphine [Japanese Patent Publication No. 60-11023 (corresponding German Patent No. 2413935) and Japanese Patent Publication No. 61-2660 (corresponding German Patent No. 2541855], and also anti-depressive action (Curr Ther Res. 1985;38:23-29).

The present inventors have found that rolipram, in any form of ($\pm$), (+) and (−) compounds, is effective as an anti-dementia agent.

The present invention also claims the applications of the drug for improving the main symptoms of dementia, including defects of memory, disorientation, disturbance in abstract thinking, and fall in judgment, and further symptoms accompanying them, such as nocturnal delirium, hallucination, wandering, depersonalization, etc.

Specific examples of diseases to which the drug of the present invention is applicable include cerebro-vascular dementia represented by multiple infarct dementia and amyloid angiopathic dementia, cerebro-parenchymatous dementia represented by Alzheimer dementia and Pick's disease and dementia caused by brain tumor, hydrocephalus, hepatic meningitis, cerebral trauma, etc., dementia caused by cerebral function disorders, and various other symptoms accompanying these dementia.

ACUTE TOXICITY

The results of mouse acute toxicity test of rolipram are as follows.

|  | Route for Administration | $ED_{50}$ Value |
|---|---|---|
| ($\pm$) Rolipram | i.p. | 1500 mg/kg |
|  | p.o. | 4000 mg/kg |
| (+) Rolipram | i.p. | >2300 mg/kg |
|  | p.o. | >4000 mg/kg |
| (−) Rolipram | i.p. | 2300 mg/kg |
|  | p.o. | 4000 mg/kg |

METHOD AND DOSE

A daily dose of the drug of the present invention to be administered p.o. to adult is in a range of 0.001 to 10 mg calculated as the effective ingredient in a range of 0.001 to 10 mg, preferably 0.01-3 mg calculated as the effective ingredient. The anti-dementia agent of the invention advantageously comprises (−) rolipram, either in the form of the ($\pm$) racemic mixture or substantially free of (+) rolipram. The daily dose may then advantageously be 0.001 to 5 mg, calculated as (−) rolipram.

To form the compound of the present invention into pharmaceutical preparations, conventional methods in the field of making pharmaceutical preparations are employed. The form of oral administration is not particularly limited, but examples are tablets, granules, powders or capsules or in liquid form. More specifically, after adding excipients and further if necessary, binders, disintegrators, lubricants, coloring matters, etc. to the main ingredient, the mixture is formed into pharmaceutical preparations such as tablets, coated tablets, granules, powders or capsules in a conventional manner. The drugs of the present invention can also be applied in parental administration. In parenteral administration, the drugs are applied in solution or suspension.

EXAMPLES

Example 1

Activity on survival time of mouse in oxygen-short state

Mice were put in a plastic box of 150 cm each in length, width and height, and carbon dioxide was injected from a lower inlet at a rate of 500 ml/min. The period from the start of injection to the respiratory standstill of mice was counted as the survival time. ($\pm$) Rolipram, (+) rolipram, and (−) rolipram were all intraperitoneally administered to mice 30 minutes before carbon dioxide was loaded.

The results are shown in Table 1.

TABLE 1

| Treatment | Survival Time (Second) |
|---|---|
| Control | 195.8 $\pm$ 3.7 |
| ($\pm$) Rolipram$_{(1.0\ mg/kg)}$ | 220.3 $\pm$ 6.9 |
| (+) Rolipram$_{(3.0\ mg/kg)}$ | 217.2 $\pm$ 5.3 |
| (−) Rolipram$_{(0.3\ mg/kg)}$ | 219.8 $\pm$ 6.3 |

($\pm$) Rolipram, (+) rolipram, and (−) rolipram showed the action of prolonging the survival time in doses of 1.0 mg/kg, 3.0 mg/kg and 0.3 mg/kg, respectively.

Example 2

Test on memory and study of rat using radial maize

Rats under feed control were put at the central platform (diameter: 25 cm) of an 8-way radial maize (length and width of arm: 48 cm and 10 cm, 40 cm, height from the ground) and trained until they could efficiently take the feed put on the tip of the arm. Numbers of correct choices for the arms where the rats reached for the first time, number of incorrect choices for the arms where the rats reached two or more times and running time until completion of the session were measured for 10 minutes at maximum. When the results with not less than 7 correct choices were shown in 3 continuous sessions it was estimated that acquirement of space recognition was completed. Space recognition disorder was induced in the rats by administering 0.5 mg/kg of scopolamine (i.p., 30 minutes before the session) to study each activity of (±) rolipram, (+) rolipram and (−) rolipram (all administered p.o., 60 minutes before the session).

The results are shown in Table 2.

(±) Rolipram, (+) rolipram and (−) rolipram showed the activity of improving space recognition disorders, defined as a decrease in the number of correct choices and increase in the number of incorrect choices, induced by scopolamine in doses of 0.02, 10 and 0.01 mg/kg, respectively.

TABLE 2

| Treatment | Number of Correct Choice | Number of Incorrect Choice |
|---|---|---|
| Control | 7.9 ± 0.2 | 0.3 ± 0.1 |
| Scopolamine 0.5 mg/kg | 5.9 ± 0.2 | 7.1 ± 0.9 |
| + (±) Rolipram 0.02 mg/kg | 6.9 ± 0.2 | 2.3 ± 1.1 |
| + (+) Rolipram 10 mg/kg | 7.2 ± 0.3 | 2.3 ± 1.6 |
| + (−) Rolipram 0.01 mg/kg | 6.9 ± 0.3 | 3.2 ± 1.1 |

Example 3

Test on memory and learning of rats using 3-panel runway device

A 3-panel runway device (length: 175 cm, width: 36 cm and height: 25 cm) comprises a start box, four gateways equipped with three-panel gates and a goal box in which feed are put as the reward. The panel gates were designed so that only one of three panel gates in each gateway might be passable. Training of hungry rats to go out of the start box, reach the goal box and take the feed was made by continuous 6 sessions in 2 minute intervals. The training was carried out every day with the passable panel gate being varied every day. In the test, (1) time taken for the rat to reach the goal box and take the feed after it left the start box, and (2) the number of incorrect choices that the rat made trying to pass the impassable gate were recorded and measured in each session. Rats satisfying for consecutive 3 days the criterion that the total time for 6 sessions in one day was within 60 seconds, the total number of incorrect choices was under 12 and the number of incorrect responses in sessions 2 to 6 was not greater than 8 were estimated to have completely learned. The rats are used for the following test.

1) Activity against memory and learning disorders induced by scopolamine

The activity of each of (±) rolipram, (+) rolipram and (−) rolipram against memory and learning disorders induced by 0.56 mg/kg of scopolamine (all were administered i.p. 15 minutes before the initiation of session) was examined.

The results are shown in Table 3 (numerals denote the number of incorrect responses).

(±) Rolipram, (+) rolipram and (−) rolipram inhibited the increase in the number of incorrect responses induced by scopolamine with doses of 0.1 mg/kg, 1 mg/kg and 0.032 mg/kg, respectively.

TABLE 3

| Treatment | Session | | | | | |
| | 1 | 2 | 3 | 4 | 5 | 6 |
|---|---|---|---|---|---|---|
| Control | 3.08 ± 0.23 | 1.89 ± 0.26 | 1.03 ± 0.19 | 0.68 ± 0.14 | 0.29 ± 0.09 | 0.42 ± 0.11 |

TABLE 3-continued

| Treatment | Session | | | | | |
| | 1 | 2 | 3 | 4 | 5 | 6 |
|---|---|---|---|---|---|---|
| Scopolamine 0.56 mg/kg | 6.21 ± 0.49 | 4.74 ± 0.38 | 3.24 ± 0.33 | 3.11 ± 0.34 | 2.68 ± 0.27 | 2.32 ± 0.25 |
| + (±) Rolipram 0.1 mg/kg | 5.67 ± 0.95 | 3.00 ± 0.73 | 1.67 ± 0.61 | 1.00 ± 0.45 | 1.00 ± 0.63 | 1.17 ± 0.48 |
| + (+) Rolipram 1 mg/kg | 4.00 ± 1.10 | 4.17 ± 0.87 | 3.00 ± 0.68 | 2.00 ± 0.52 | 1.83 ± 0.65 | 1.67 ± 0.61 |
| + (−) Rolipram 0.032 mg/kg | 4.50 ± 0.43 | 2.67 ± 0.84 | 1.50 ± 0.56 | 1.50 ± 0.72 | 1.17 ± 0.54 | 0.50 ± 0.22 |

2) Effect on cerebral ischemia-induced learning and memory disorders

According to the method of Pulsinelli et al., the both vertebral arteries of rat were burnt and cut under anesthesia with pentobarbital. After 24 hours, the whole carotid artery on both sides was blocked for 5 minutes under no anesthesia. The effect of (±) rolipram, (+) rolipram and (−) rolipram (i.p. administered immediately after resuming blood flow and 30 minutes before starting the session) on deficits of learning and memory was examined.

The results are shown in Table 4 (numerals denote the number of incorrect responses).

(±) Rolipram and (−) rolipram improved the disorders induced by cerebral ischemia in doses of 0.1 mg/kg and 0.032 mg/kg, respectively. However, (+) rolipram showed no improvement in a dose of 1 mg/kg.

From the foregoing experimental results using mice and rats, it is evident that (±) rolipram, (+) rolipram and (−) rolipram showed the activity of improving memory and learning deficits. The potency in the activity was in the more potent order of (−) rolipram, (±) rolipram and (+) rolipram. Further, it is noted that all of (±) rolipram, (+) rolipram and (−) rolipram are highly safe.

According to the present invention, an anti-dementia agent with a high safety can be provided.

TABLE 4

| Treatment | Session | | | | | |
| | 1 | 2 | 3 | 4 | 5 | 6 |
|---|---|---|---|---|---|---|
| Control | 4.00 ± 0.71 | 1.80 ± 0.49 | 1.20 ± 0.37 | 1.20 ± 0.37 | 0.40 ± 0.40 | 0.60 ± 0.40 |
| Cerebral ischemia | 5.09 ± 0.49 | 3.36 ± 0.45 | 2.64 ± 0.49 | 2.18 ± 0.44 | 2.27 ± 0.41 | 2.18 ± 0.50 |
| + (±) Rolipram 0.1 mg/kg | 4.25 ± 0.45 | 3.00 ± 0.42 | 2.88 ± 0.23 | 1.88 ± 0.44 | 1.38 ± 0.32 | 1.13 ± 0.35 |
| + (+) Rolipram 1 mg/kg | 5.33 ± 1.15 | 3.67 ± 0.56 | 2.00 ± 0.52 | 2.83 ± 1.08 | 1.67 ± 0.61 | 1.50 ± 0.96 |
| + (−) Rolipram 0.032 mg/kg | 5.50 ± 1.34 | 2.00 ± 0.52 | 2.00 ± 0.68 | 1.33 ± 0.56 | 1.00 ± 0.26 | 0.83 ± 0.31 |

We claim:

1. A method for the treatment of dementia, comprising administering to a host in need of such treatment an effective amount of a compound of the formula

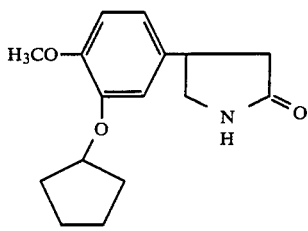

2. A method according to claim 1, wherein the dementia is cerebro-vascular dementia, cerebro-parenchymatous dementia, or dementia caused by brain tumor, hydrocephalus, hepatic meningitis, or cerebral trauma.

3. A method according to claim 2, wherein the dementia is multiple infarct dementia, amyloid angiopathic dementia, Alzheimer's dementia, or Pick's disease.

4. A method according to claim 1, wherein the compound is (−)rolipram or (±)rolipram.

5. A method according to claim 1, wherein the compound is (+)rolipram.

6. A method for the treatment of memory defects, disorientation, nocturnal delirium, or hallucination in a host in need of such treatment, comprising administering an effective amount of a compound of the formula

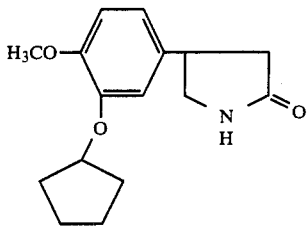

7. A method according to claim 6, wherein the compound is (−)rolipram or (±)rolipram.

8. A method according to claim 6, wherein the compound is (+)rolipram.

* * * * *